United States Patent
Peppers

(10) Patent No.: US 8,177,821 B2
(45) Date of Patent: May 15, 2012

(54) SCREW BACK-OUT PREVENTION MECHANISM

(76) Inventor: Timothy Allen Peppers, LaJolla, CA (US)

( * ) Notice: Subject to any disclaimer, the term of this patent is extended or adjusted under 35 U.S.C. 154(b) by 889 days.

(21) Appl. No.: 12/180,787

(22) Filed: Jul. 28, 2008

(65) Prior Publication Data

US 2009/0062863 A1    Mar. 5, 2009

Related U.S. Application Data

(60) Provisional application No. 60/952,161, filed on Jul. 26, 2007.

(51) Int. Cl.
*A61B 17/80* (2006.01)

(52) U.S. Cl. .......................................... 606/289

(58) Field of Classification Search .................. 606/289, 606/290, 295, 296; 411/372.5
See application file for complete search history.

(56) References Cited

U.S. PATENT DOCUMENTS

| | | | |
|---|---|---|---|
| 7,004,944 B2 * | 2/2006 | Gause | 606/294 |
| 7,306,605 B2 * | 12/2007 | Ross | 606/70 |
| 7,452,370 B2 * | 11/2008 | Anderson | 606/296 |
| 7,662,174 B2 * | 2/2010 | Doubler et al. | 606/289 |
| 2006/0149255 A1 * | 7/2006 | Doubler et al. | 606/69 |

* cited by examiner

*Primary Examiner* — Nicholas Woodall
(74) *Attorney, Agent, or Firm* — Kauth, Pomeroy, Peck & Bailey LLP

(57) ABSTRACT

A screw back-out prevention mechanism for a bone fixation system is provided. The mechanism, when engaged, either locks or retains the screws of the bone fixation system in place thereby preventing the screws of the bone fixation system from backing out of the bone, and in turn reducing the risk of device separation or failure in the bone fixation system.

13 Claims, 7 Drawing Sheets

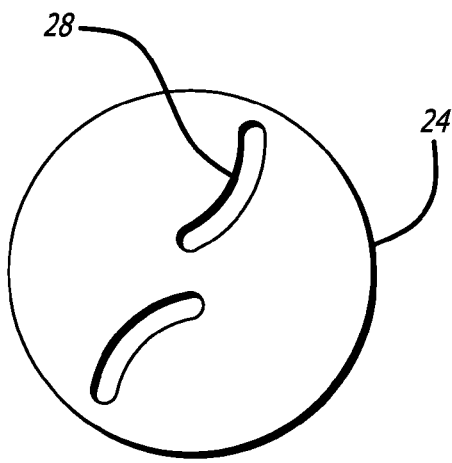
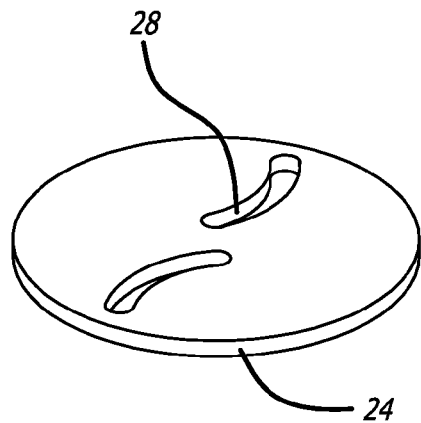
*FIG. 3a*          *FIG. 3b*
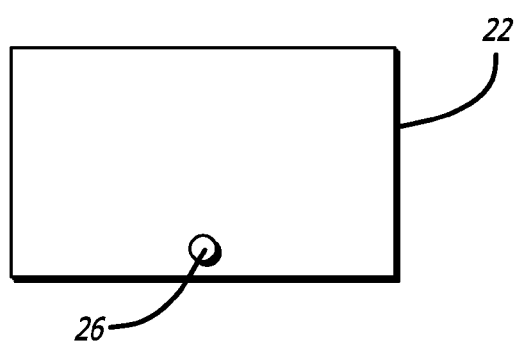
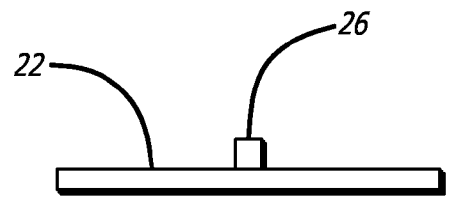
*FIG. 3c*          *FIG. 3d*

SCREW BACK-OUT PREVENTION MECHANISM

CROSS-REFERENCE TO RELATED APPLICATIONS

The current application claims priority to U.S. Provisional Application No. 60/952,161, filed Jul. 26, 2007, the disclosure of which is incorporated herein by reference.

FIELD OF THE INVENTION

The current invention is directed to a mechanism for preventing the back-out of a screw; and more particularly for a mechanism for preventing the back-out of screws in a bone fixation device.

BACKGROUND OF THE INVENTION

The use of fixation plates for the treatment of bone fusions and fixations has grown more prevalent over the past decade. Indeed, while early procedures using fixation plates were generally restricted to long bones and lower lumbar levels of the spine, fixation plates have increasingly found applications in other bone instrumentation such as in the cervical spine.

A typical bone fixation plate is provided with a plurality of bores therethrough. A corresponding plurality of fastener members, typically bone screws having a headed portion and a threaded shaft, are provided to secure the plate to the bone, or bones, to be fixated. A common problem with the use of fixation plates, regardless of their location, is the tendency of the bone screws to "back-out" of the underlying bone. This problem is particularly prevalent in areas of high stress such as the spine. Given the delicate nature of the spine, anything that may result in post-operative complications, such as plate movement or revision, can seriously endanger the patient's long-term prognosis.

Bone fixation systems have employed various techniques in an attempt to overcome the problem of screw back-out. Current techniques rely either on the use of specially designed bone screws, are irreversible, or require special procedures that could complicate the surgery. For example, U.S. Pat. No. 5,275,601 discloses a self-locking bone fixation system wherein the heads of the bone screws are frustoconical in shape and have a directionally corrugated outer surface; U.S. Pat. No. 5,269,784 discloses a threaded screw nut that threadingly engages a portion of the bone screw to thereby secure the bone screw to the fixation plate; U.S. Pat. No. 4,484,570 discloses a bone fixation system wherein the heads of the bone screws are hollow and expandable; and U.S. Pat. No. 5,578,034 discloses a bone fixation system in which the plates are heated after insertion, thereby expanding a retaining mechanism into place around the screw.

All of the cited prior art systems suffer from one or more undesirable drawbacks. First, some of these prior art systems rely on a retainer that itself uses a threaded connection to maintain the bone screws in position, meaning that the problem of screw back-out still exists. Second, several of these systems permanently seal the screw into place, rendering revision or alteration of the plate very difficult. Finally, the requirement that one use a particular, specially designed proprietary bone screw to prevent back-out limits a surgeon's ability to choose the best-engineered screw for a particular application because the proprietary bone screw may have inappropriate specifications such as thread pitch. Accordingly, a bone fixation system incorporating a mechanism for preventing screw back-out that is simple to use and revise and can be operated with any standard bone screw would be desirable.

SUMMARY OF THE INVENTION

The current invention is generally directed to a screw back-out prevention device. The device generally comprises at least one moveable element and a rotary activation element that interlockingly engages such that the rotation of the rotary activation element causes the at least one moveable element to advance into a lock position where the back-out of the screw is prevented.

In one embodiment of the screw back-out prevention device of the current invention the moveable plates and the rotary element are engaged together via an interlocking pin and curvilinear slot.

In another embodiment the screw back-out prevention device of the current invention operates in cooperation with a bone fusion device. In such an embodiment, the device may either be integrated into the body of the fusion device or attached to a top surface of a bone fusion device.

In still another embodiment of the screw back-out prevention device of the current invention the rotary activation element is removably engaged to the at least one moveable plate.

In yet another embodiment the screw back-out prevention device of the current invention operates by covering the exposed surface of the head of the screw when in the lock position.

In still yet another embodiment the screw back-out prevention device of the current invention operates by engaging a portion of the screw in the lock position. In such an embodiment, the device of the current invention either directly or indirectly engages the screw. In the embodiment of the current invention where the device indirectly engages the screw it may do so through a retention ring that may either be integrated into a screw or disposed within the bone fusion plate itself.

In still yet another embodiment the screw back-out prevention device of the further invention operates through at least one cam designed to rotate into locking engagement with at least a portion of the screw.

In still yet another embodiment, the screw back-out prevention device of the current invention is formed from a material selected from the group consisting of Ti, stainless steel and NiTi.

BRIEF DESCRIPTION OF THE FIGURES

The description will be more fully understood with reference to the following figures, which are presented as exemplary embodiments of the invention and should not be construed as a complete recitation of the scope of the invention, wherein:

FIG. 3 shows schematic diagrams of the individual components of the screw back-out prevention mechanism shown in FIGS. 2a and b;

DETAILED DESCRIPTION OF THE INVENTION

The current invention is directed generally to a mechanism for preventing screw back-out in a bone fixation system. The back-out prevention device of the current invention uses a plurality of moveable components to directly or indirectly engage the screws of the bone fixation system to either lock or retain the screws into a specific position within the overall bone fixation system.

Figure 1A:
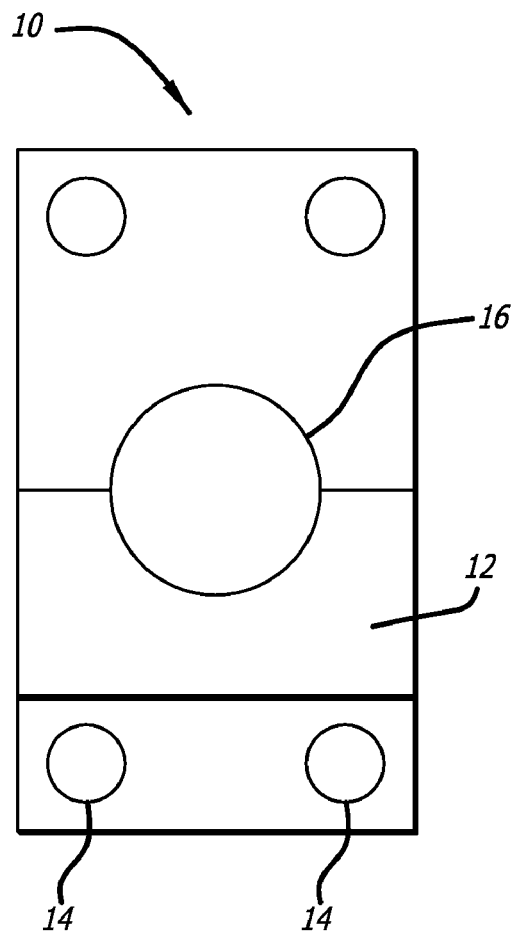
FIGS. 1a and 1b provide schematic diagrams of a screw back-out prevention device in accordance with the current invention.
Figure 1B:
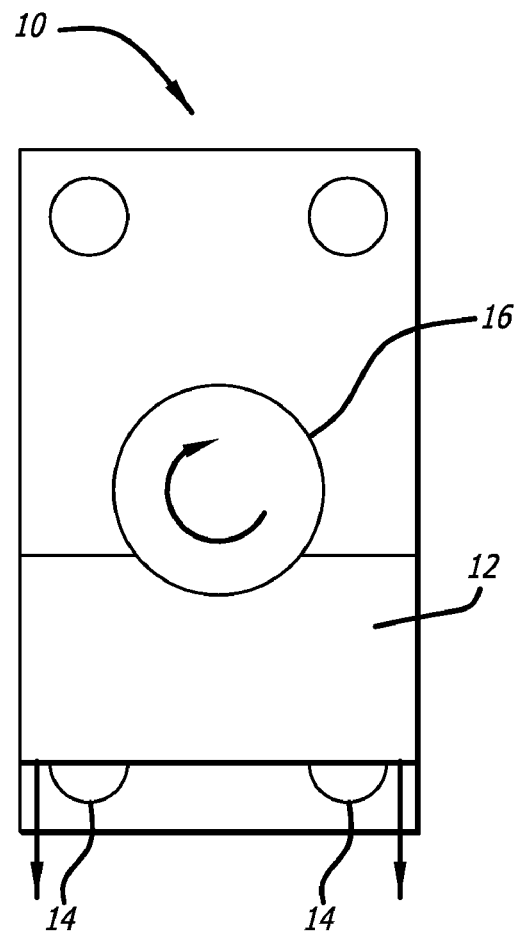

A generic schematic of the screw back-out prevention device is provided in FIG. 1. As shown, the device (10) generally comprises at least one moveable component (12) that can be compelled either directly or indirectly to lock or retain the screw (14) into a desired position by the operation of a second rotary activation element (16).

Figure 2A:
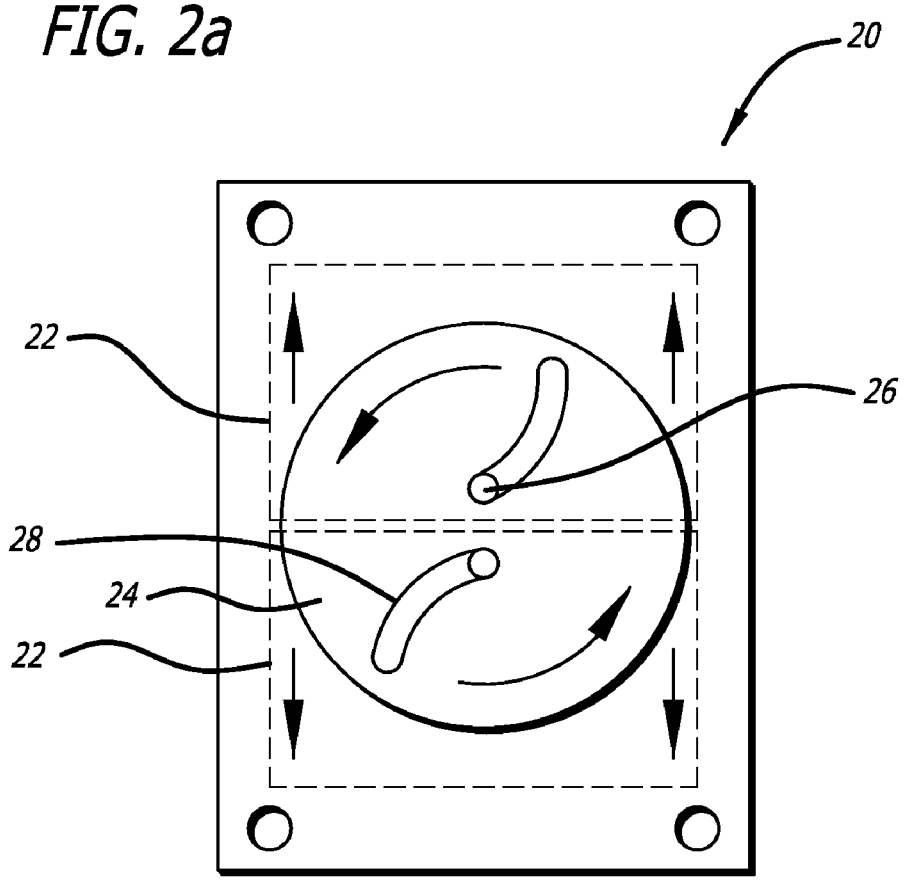
FIGS. 2a and 2b provide top and side view schematic diagrams of a spinal fixation plate incorporating a screw back-out prevention mechanism in accordance with one exemplary embodiment of the current invention.
Figure 2B:
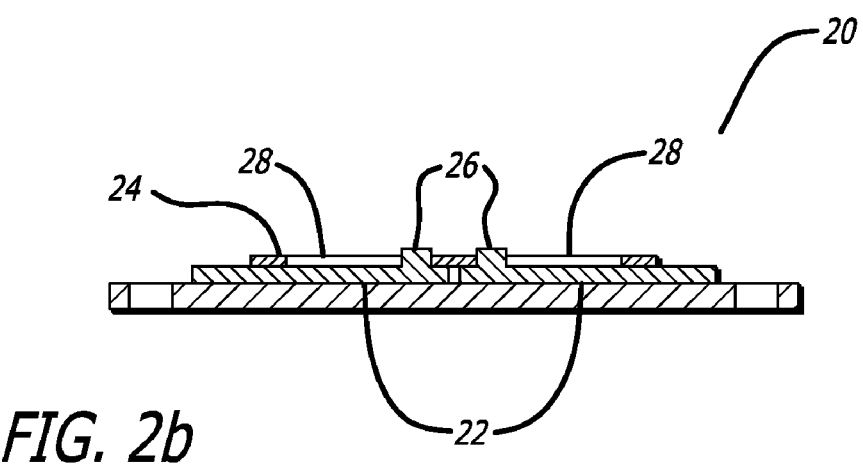

An exemplary embodiment of the screw back-out prevention system of the current invention is shown schematically in FIGS. 2 and 3. In this first exemplary embodiment, the device (20) comprises two moveable plates (22) and a rotary component (24) for engaging and moving the moveable plates into and out of screw retention/locking alignment. In the embodiment shown best in FIG. 3, the plates (22) have a pair of pins (26) that are designed to engage a pair of cooperative curvilinear slots (28) on the rotary component (24). As shown in FIGS. 2a and 2b, when the rotary element (24) is rotated the curvilinear slots (28) apply a force to the pins (26), which in turn direct the movement of the plates. The direction and distance of the movement of the plates (22) are controlled by the shape of the curvilinear slots (28) and the direction of rotation applied to the rotary component (24). As shown in FIGS. 2 and 3, in the current embodiment the counter-clockwise rotation of the rotary component (24) imparts a motion in the outward direction to the moveable plates (22). It should be understood, however, that the direction imparted can be reversed without altering the function of the current invention.

Figure 4A:
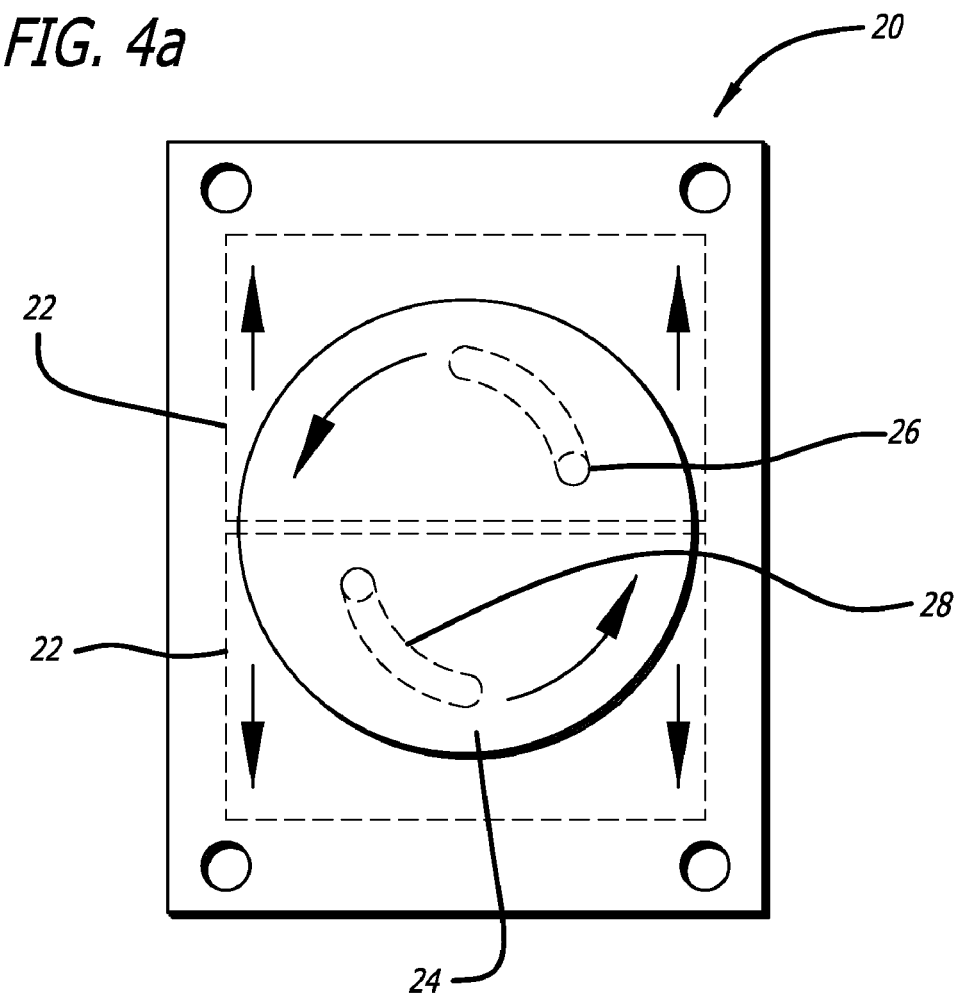
FIGS. 4a and 4b provide top and side view schematic diagrams of a spinal fixation plate incorporating a screw back-out prevention mechanism in accordance with one exemplary embodiment of the current invention.
Figure 4B:
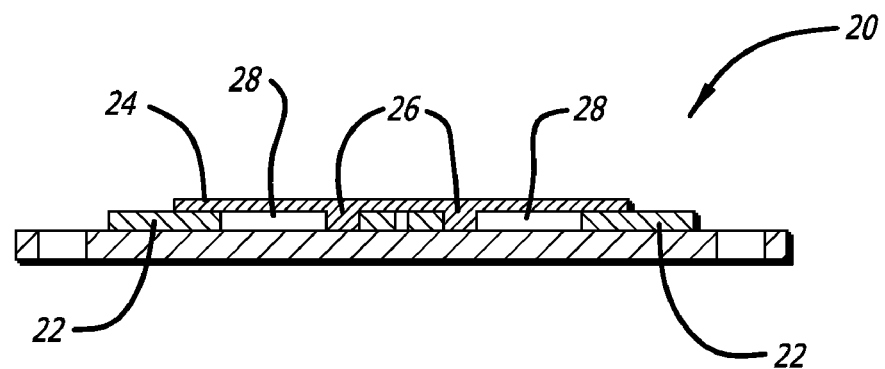
Figure 5A:
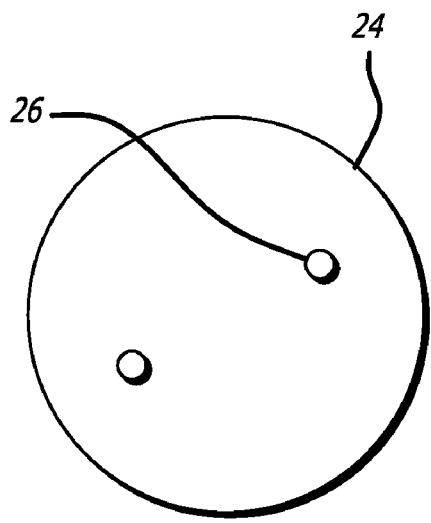
FIG. 5 shows schematic diagrams of the individual components of the screw locking/retention mechanism shown in FIGS. 4a and b.
Figure 5B:
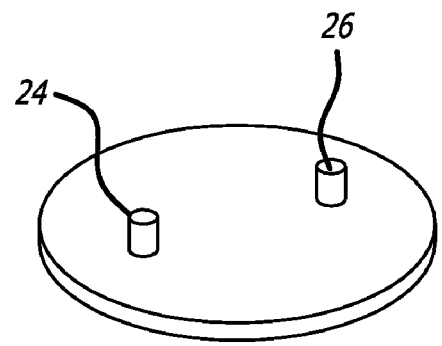
Figure 5C:
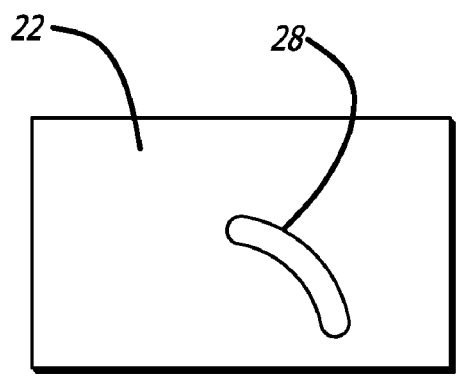
Figure 5D:
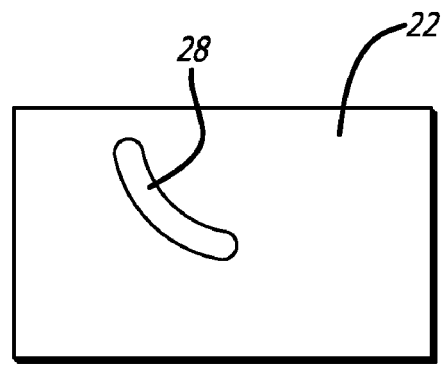

Although the embodiment shown in FIGS. 2 and 3 are designed such that the rotary component (24) is slotted and the moveable plates (22) have pins, an opposite arrangement, as shown in FIGS. 4 and 5 would be equally acceptable. Specifically, as shown in FIG. 5, in a second exemplary embodiment of the device the pins (26) are disposed on the rotary component (24) and the curvilinear slots (28) are disposed on the moveable plates (22). Moreover, although only single pin/slot combinations are shown, it should be understood that any number of pins may be made to engage the curvilinear slots of the rotary component.

FIGS. 1 to 5 show a number of schematic diagrams of exemplary embodiments of the back-out prevention device of the current invention and the arrangement of the main components thereof; however, it should be understood that the manner in which the moveable components of the device prevent screw back-out may themselves take a number of different forms. Schematic diagrams showing exemplary mechanisms are provided in FIGS. 6 to 9.

Figure 6A:
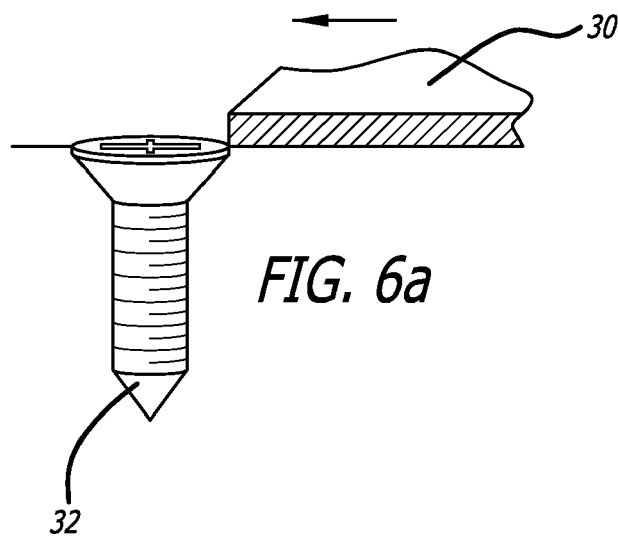
FIGS. 6 to 9 provide schematic diagrams of the various mechanisms of operation of several exemplary embodiments of the screw back-out prevention mechanism in accordance with the current invention.
Figure 6B:
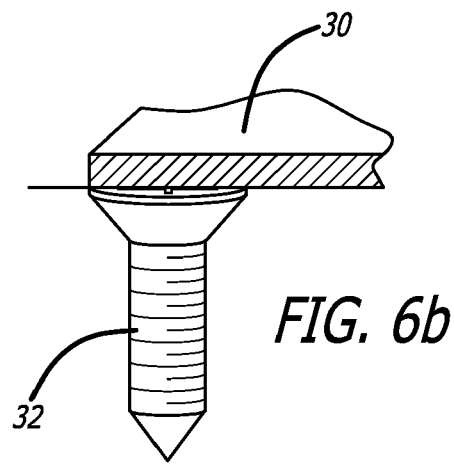

FIGS. 6a and 6b provide schematic diagrams showing the mechanism of operation of a first embodiment of the screw back-out prevention device of the current invention. In this embodiment the moveable plate (30) is positioned relative to the screw (32) such that when moved into the screw retention position (FIG. 6b) the plate covers the head of the bone screw, thereby preventing the screw from backing out of the bone fixation plate.

Figure 7A:
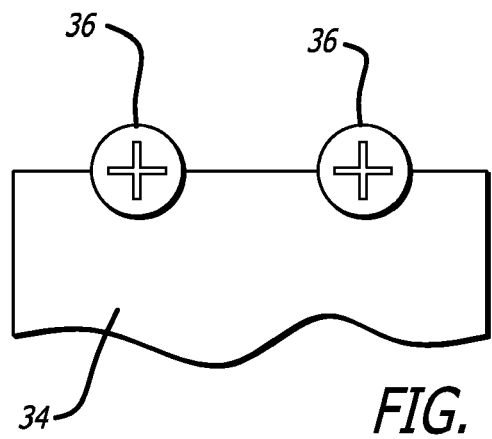
Figure 7B:
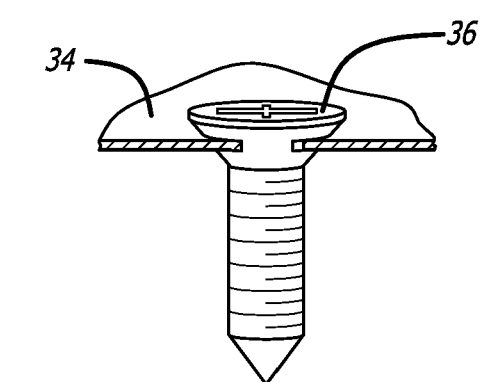

FIGS. 7a and 7b provide schematic diagrams of the mechanism of operation of a second embodiment of the screw back-out prevention device of the current invention. In this embodiment, the moveable plate (34) directly engages an interlock portion of the screw (36) specifically designed for such a function.

Figure 8:
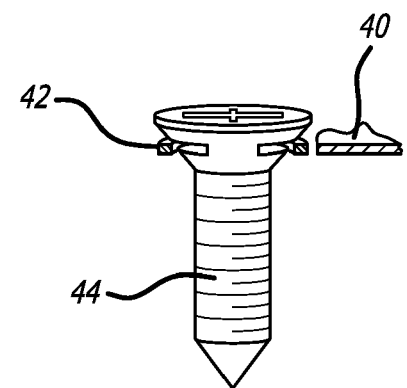

FIG. 8 provides a schematic diagram of the mechanism of operation of a third embodiment of the screw back-out prevention device of the current invention. In this embodiment, the moveable plate (40) engages a retention ring (42) positioned either on the screw itself or within the bone fixation plate. The retention ring (42) then directly engages an interlock portion of the screw (44) specially designed for such a function.

Although in the embodiments shown in FIGS. 7 and 8 the interlock portion of the screws (36 & 44) take the form of slots designed to interact with the moveable plate or retention ring, it should be understood that the engagement portion may take any shape or form suitable to receive a portion of the moveable plate thereby securing the screw into position. Examples of suitable engagement portions may include, for example, a hole and pin.

Figure 9:
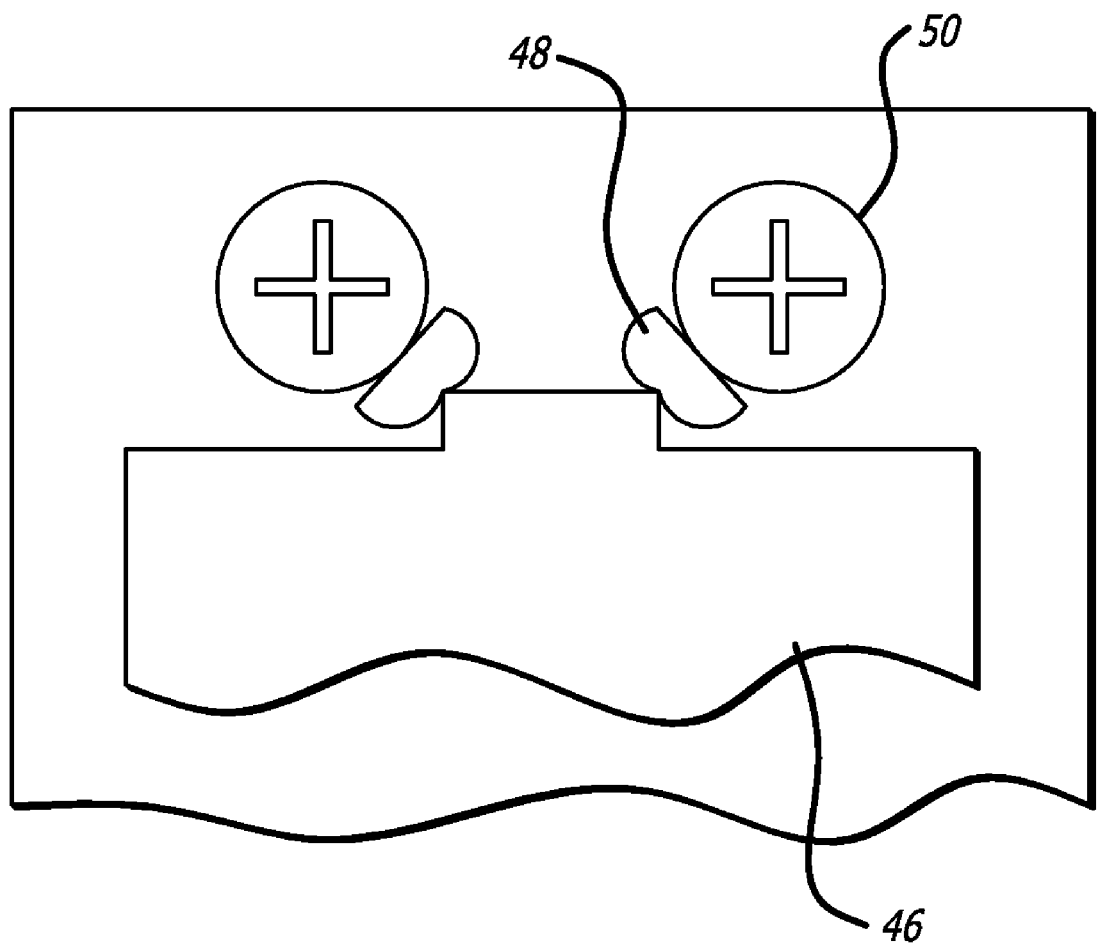

Finally, FIG. 9 provides a schematic diagram of the mechanism of operation of a fourth embodiment of the screw back-out prevention device of the current invention. In this embodiment, the moveable plate (46) engages a cam mechanism (48) that rotates when activated by the moveable plates to engage a portion of the screw (50) thereby locking the screw into place.

Regardless of the actual design of the screw back-out prevention device and its manner of operation, it should be understood that a further locking mechanism may be included in its design to ensure that once engaged in the locked position the moveable elements cannot be inadvertently moved out of said position. In a preferred embodiment, the locking mechanism is designed to be reversibly engaged such that the back-out prevention device can be unlocked if necessary, such as, for example, for revision or removal of the bone fusion system. However, such a locking mechanism may take any suitable form, including, for example, a blocking element inserted between the moveable plates to prevent movement in the reverse direction, a set screw, pin, etc.

Although all of the above figures and the accompanying descriptive text, have focused only on the arrangement of the main components of the screw back-out prevention device of the current invention, it should be understood that the device can either be integrated into a bone fixation plate, such as a spinal fusion plate, or attached to the top of a plate such that the it can retain or lock the screws of the bone fixation plate into place. If the screw back-out prevention device is attached to the top of a bone fixation plate, the attachment may be either permanent or temporary, i.e., the device may be integrally affixed to the plate such as by welding, or can be removably attached such as by screws or other removable fasteners. In addition, the rotary component may either be permanently integrated with the moveable plates, or may be a separate tool that is engaged with the moveable plates only during the operation of the device. In such an embodiment, the rotary component would be engaged with the posts or curvilinear slots of the moveable plates, depending on the device's design, the moveable plates would be engaged to lock the bone fixation screws into place, and then the rotary component would be removed.

As has been previously discussed, the device can be incorporated into or added on to any conventional bone fixation plate that uses bone screws as the means of attaching the plate to the bone. However, the device may also be used in other building, construction or home use/repair systems and devices where screw back-out may be an issue.

The components of the screw back-out prevention device of the current invention, and any bone fixation plate into which the device is incorporated, may be formed of any conventional surgical material. Exemplary conventional materials include, for example, titanium and stainless steel. In addition, portions of the device may be made of memory metals or smart memory alloys, such as, for example, NiTi. In particular, these smart memory alloys are particularly suitable for use in making the retention rings used in some embodiments of the invention.

It should be clear to one of ordinary skill in the art that the drawings provided in the current application are only meant to be schematic, and the size and shape of the slots, posts and other components of the screw back-out prevention device should be designed to ensure that the moveable plates can be positioned to engage or retain the screws for which back-out prevention is desired.

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A screw back-out prevention device comprising:
   at least one moveable element having at least one first cooperative member disposed on a surface thereof, said moveable element being disposed adjacent to at least one screw having a head and an elongated threaded shaft;
   a rotary activation element having at least one second cooperative member disposed on a surface thereof;
   wherein said at least one first cooperative member and the at least one second cooperative member are designed to interlockingly engage such that the rotation of the rotary activation element causes the at least one moveable element to advance into a lock position in which the moveable element is disposed such that movement of the screw in the direction of the head of the screw results in the application of a normal. force to the screw in a direction parallel to the axis of the elongated threaded shaft by the moveable element thereby restricting said movement of the screw.

2. The screw back-out prevention device of claim 1, wherein the first cooperative member is a pin and the second cooperative member is a curvilinear slot.

3. The screw back-out prevention device of claim 1, wherein the first cooperative member is a curvilinear slot and the second cooperative member is a pin.

4. The screw back-out prevention device of claim 1, wherein the at least one moveable element comprises at least two slidable plates arranged to lock a plurality of screws.

5. The screw back-out prevention device of claim 1, wherein the device is integrated into a bone fusion device.

6. The screw back-out prevention device of claim 1, wherein the device is attached to a top surface of a bone fusion device.

7. The screw back-out prevention device of claim 1, wherein the rotary activation element is removably engaged with the at least one moveable plate.

8. The screw back-out prevention device of claim 1, wherein the device is formed from a material selected from the group consisting of Ti, stainless steel and NiTi.

9. A bone fusion system comprising:
   a bone fusion plate having at least one hole passing therethrough;
   at least one fixation screw designed to pass through said hole of said bone fusion plate to anchor said plate to a bone; and
   a screw back-out prevention device, itself comprising:
      at least one moveable element having at least one first cooperative member disposed on a surface thereof, said moveable element being disposed adjacent to at least one screw having a head and an elongated threaded shaft,
      a rotary activation element having at least one second cooperative member disposed on a surface thereof, and
      wherein said at least one first cooperative member and the at least one second cooperative member are designed to interlockingly engage such that the rotation of the rotary activation element causes the at least one moveable element to advance into a lock position in which the moveable element is disposed such that movement of the screw in the direction of the head of the screw results in the application of a normal. force to the screw in a direction parallel to the axis of the elongated threaded shaft by the moveable element thereby restricting said movement of the screw.

10. The bone fusion system of claim 9, wherein the first cooperative member is a pin and the second cooperative member is a curvilinear slot.

11. The bone fusion system of claim 9, wherein the first cooperative member is a curvilinear slot and the second cooperative member is a pin.

12. The bone fusion system of claim 9, wherein the at least one moveable element comprises at least two slidable plates arranged to lock a plurality of screws.

13. The bone fusion system of claim 9, wherein the rotary activation element is removably engaged with the at least one moveable plate.

* * * * *

UNITED STATES PATENT AND TRADEMARK OFFICE
CERTIFICATE OF CORRECTION

PATENT NO. : 8,177,821 B2
APPLICATION NO. : 12/180787
DATED : May 15, 2012
INVENTOR(S) : Timothy Allen Peppers Page 1 of 1

It is certified that error appears in the above-identified patent and that said Letters Patent is hereby corrected as shown below:

Col. 5, in claim 1, line 50, after "normal" delete ".".

Col. 6, in claim 9, line 40, after "normal" delete ".".

Signed and Sealed this
Tenth Day of July, 2012

David J. Kappos
*Director of the United States Patent and Trademark Office*